United States Patent
Masson et al.

(10) Patent No.: US 9,747,416 B2
(45) Date of Patent: Aug. 29, 2017

(54) TRANSACTIONAL STORAGE SYSTEM FOR HEALTHCARE INFORMATION

(75) Inventors: Arnaud Masson, Nancy (FR); Romain Demoustier, Nice (FR)

(73) Assignee: MERGE ECLINICAL, INC., Hartland, WI (US)

( * ) Notice: Subject to any disclaimer, the term of this patent is extended or adjusted under 35 U.S.C. 154(b) by 336 days.

(21) Appl. No.: 13/081,062

(22) Filed: Apr. 6, 2011

(65) Prior Publication Data

US 2011/0276605 A1    Nov. 10, 2011

Related U.S. Application Data

(63) Continuation of application No. 12/160,485, filed as application No. PCT/IB2006/003156 on Jul. 17, 2006, now abandoned.

(51) Int. Cl.

| | |
|---|---|
| G06F 17/30 | (2006.01) |
| G06F 19/00 | (2011.01) |
| G06Q 10/10 | (2012.01) |
| G06Q 40/08 | (2012.01) |
| G06Q 50/22 | (2012.01) |

(52) U.S. Cl.
CPC ........ G06F 19/327 (2013.01); G06F 17/3023 (2013.01); G06F 17/30144 (2013.01); G06F 19/328 (2013.01); G06F 19/366 (2013.01); G06Q 10/10 (2013.01); G06Q 40/08 (2013.01); G06Q 50/22 (2013.01)

(58) Field of Classification Search
None
See application file for complete search history.

(56) References Cited

U.S. PATENT DOCUMENTS

| | | | | |
|---|---|---|---|---|
| 5,956,489 | A  * |  9/1999 | San Andres et al. | 709/221 |
| 5,991,772 | A  * | 11/1999 | Doherty et al. | |
| 7,036,044 | B1 * |  4/2006 | Verma et al. | 714/19 |
| 7,082,446 | B1 * |  7/2006 | Bottomley | 707/610 |
| 7,099,897 | B2 * |  8/2006 | Huras et al. | 707/648 |
| 7,761,426 | B2 * |  7/2010 | Boyd et al. | 707/655 |
| 2002/0029290 | A1 * |  3/2002 | Burema et al. | 709/238 |
| 2002/0069192 | A1 * |  6/2002 | Aegerter | 707/1 |
| 2002/0143764 | A1 * | 10/2002 | Martin et al. | 707/8 |
| 2004/0139127 | A1 * |  7/2004 | Pofelski | 707/203 |
| 2004/0205309 | A1 * | 10/2004 | Watanabe | 711/161 |
| 2004/0267809 | A1 * | 12/2004 | East et al. | 707/104.1 |
| 2005/0102670 | A1 * |  5/2005 | Bretl et al. | 718/1 |
| 2005/0120039 | A1 * |  6/2005 | Amys et al. | 707/102 |
| 2007/0130226 | A1 * |  6/2007 | Banerjee et al. | 707/204 |
| 2007/0214191 | A1 * |  9/2007 | Chandrasekaran | 707/202 |

FOREIGN PATENT DOCUMENTS

WO    2008010012    1/2008

OTHER PUBLICATIONS

PCT/IB2006/003156 International Preliminary Report on Patentability and Written Opinion dated Jan. 20, 2009, 5 pages.

* cited by examiner

*Primary Examiner* — Charles Adams
(74) *Attorney, Agent, or Firm* — Michael Best & Friedrich LLP (57) ABSTRACT

Managing healthcare information data includes, on a computer, representing a state of a system based on the healthcare information, receiving a transaction representing a change to the system, changing the representation of the state of the system according to the transaction, and storing the transaction.

4 Claims, 8 Drawing Sheets

TRANSACTIONAL STORAGE SYSTEM FOR HEALTHCARE INFORMATION

CROSS REFERENCE TO RELATED APPLICATIONS

This application is a continuation and claims priority under 35 USC §120 to U.S. patent application 12/160,485, filed Nov. 12, 2008, which claims the benefit of International Serial No. PCT/IB2006/003156, filed Jul. 17, 2006, the contents of each of which are hereby incorporated by reference in their entirety.

TECHNICAL FIELD

This description relates to storing and retrieving healthcare product information.

BACKGROUND

Healthcare information must be accessed by developers, researchers, health care professionals, vendors, managers, insurers, and regulators, among others. The people accessing the information may have a diverse set of needs and resources and be distributed over a large geographic area. Numerous data systems may be required to interact to maintain all the required information and deliver it to the correct places at the proper times.

For managing healthcare information, current approaches include electronic data capture, large-scale databases of records, and automated systems to maintain and report the progress of the study. For compatibility between users and to comply with government requirements, such as for electronic reporting of clinical data to the FDA, extensible standards such as the Clinical Data Interchange Standards Consortium (CDISC) Operational Data Modeling (ODM) standard are used to store and model clinical data. These standards allow vendors to extend the capability of a standard model to include additional information or functionality of value to the vendor's customers. The FDA requires access to such files, and their auditing benefits from the traceability and retrieval that such standards enable.

Projects in various healthcare areas have such data tracking & reporting requirements, including clinical studies, complaints about healthcare products, treatments, or drugs, managing patient records, etc. Problems may arise when different aspects of a project use incompatible data systems and information fails to be exchanged in an efficient manner, or at all, for example if a patient sees several specialists who all use different record-keeping systems. Patient records are collected by physicians and experts to keep track of the medical activity and status of a patient, and typically require the tracking of thousands of diverse pieces of information. Clinical trials to determine the safety and efficacy of new drugs, treatments or medical devices also typically require the tracking of such information, including not only patient records, but also experimental results, progress reports, and financial information. Complaints concerning healthcare products must be closely monitored and rapidly reported and addressed. Timeliness and completeness of a manufacturer's response to such complaints, and records about that response, is critical.

As used in this application, the term "healthcare information" refers to the results or data produced by or associated with any analysis, research, or data collection aimed at evaluating, reporting or claiming information that impacts the health state of a person. "Clinical trial" refers to any study, research, trial, or investigation of the medical efficacy or safety of a medical substance or device. "Patient records" refers to the results or data produced by or associated with any analysis, research, or data collection aimed at the current or past state of a patient in regards to the medical treatments or procedure he has been subject to.

SUMMARY

In general, in one aspect, managing healthcare information data includes, on a computer, representing a state of a system based on the healthcare information, receiving a transaction representing a change to the system, changing the representation of the state of the system according to the transaction, and storing the transaction.

Implementations may include one or more of the following features.

Repeatedly, receiving a new transaction representing a new change to the system, changing the representation of the state of the system according to the new transaction, and storing the new transaction with previous transactions in a set of transactions. Representing the state of the system includes representing a system with an empty state, and repeatedly for each transaction in a set of transactions, changing the representation of the state of the system according to the transaction. Representing a state of the system corresponding to a point in time by representing a system with an empty state, and repeatedly for each transaction in a set of transactions corresponding to changes prior to the point in time, changing the representation of the state of the system according to the transaction.

Representing a state of the system corresponding to a particular transaction by representing a system with an empty state, and repeatedly for each transaction in a set of transactions preceding and including the particular transaction, changing the representation of the state of the system according to the transaction. Representing a state of a subset of the system corresponding to a point in time by representing a system with an empty state, and repeatedly for each transaction in a set of transactions corresponding to changes to the subset of the system prior to the point in time, changing the representation of the state of the system according to the transaction.

Representing the state of the system includes storing in a memory a hierarchy of elements, each element having one or more values, each value including data or a representation of one or more additional elements.

On a second computer, representing a copy of the state of the system, and whenever a transaction is added to the set of transactions, changing the copy of the state of the system according to the transaction.

The transaction includes a representation of the state of the system. The transaction includes a subset of elements including the representation of the state of the system, and a set of values corresponding to one or more elements in the subset of elements.

Storing the transaction includes adding the transaction or a functional representation of the transaction to a sequence of transactions in a storage. a storage includes one or more of a disk, a flash memory, a network storage device, a virtual storage volume. Adding the transaction to a sequence of transactions includes adding the transaction to a queue of transactions, and moving transactions from the queue of transactions to a storage. Adding the transaction to a sequence of transactions includes sending the transaction to a representation of a storage. The transaction is sent to a representation of a storage in the same manner that data would be sent to a local storage.

The healthcare information corresponds to one or more of a clinical study, an epidemiological study, information about a healthcare product, medical records, or insurance information. A transaction includes a binary file, and storing the transaction includes storing the binary file in a temporary location, assigning the binary file a unique identifier, adding the unique identifier to the transaction, storing the transaction in a storage, and storing the binary file in the storage.

Aspects may include a method, a computer or computer system for carrying out the method, software for configuring a computer to carry out the method, and other embodiments.

Advantages include improved traceability of healthcare information. For example, the historical progression of a clinical trial or its state at a specific point in time can be reconstructed to see if an event at that time should have been recognized as one that required a halt to a trial. Similarly, a history of product complaints can be reconstructed to determine the point in time where a company should have become aware of a defective product, or what circumstances can be identified in retrospect as indicating a defect, to improve future responses. As another example, by reconstructing the history of the clinical trial step by step or focusing on specific data at specific points in time, certain outcomes or other developments might also be more readily correlated with changes in protocol or in eligibility of patients for inclusion which were made during the course of a particular study.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Data Model

One way to manage a diverse amount of healthcare information data is a data model. A data model consists of a set of elements and associated values. For example, the elements of a model may include clinical trial data such as protocol definitions, users, roles, experimental results, etc. Depending on the size and complexity of the study, the elements used in the data model to represent the components of the study may be very complex themselves, including files, databases, or even additional data models. The elements could be arranged in a flat structure, in a hierarchy, or in some other arrangement. Similar models can be used to manage patient records or complaints about healthcare products.

Figure 1:
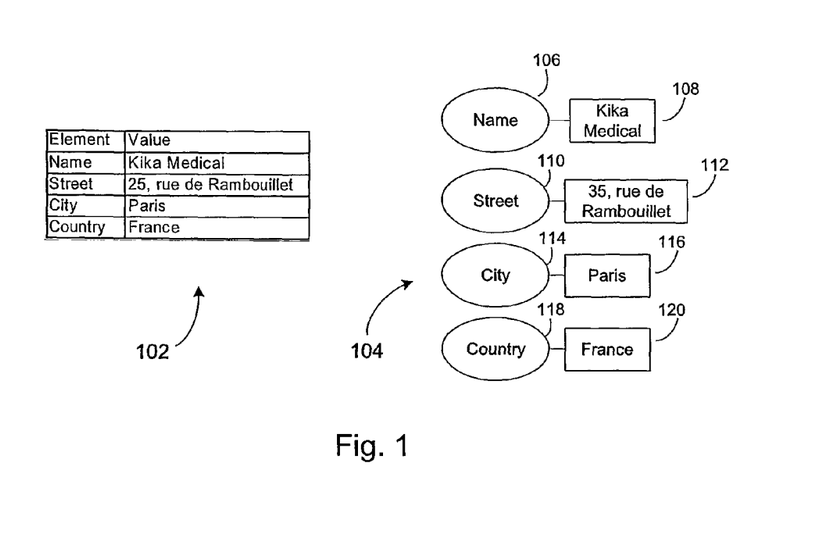
FIG. 1 is an example of model data expressed in tabular form and a corresponding block diagram.
Figure 2:
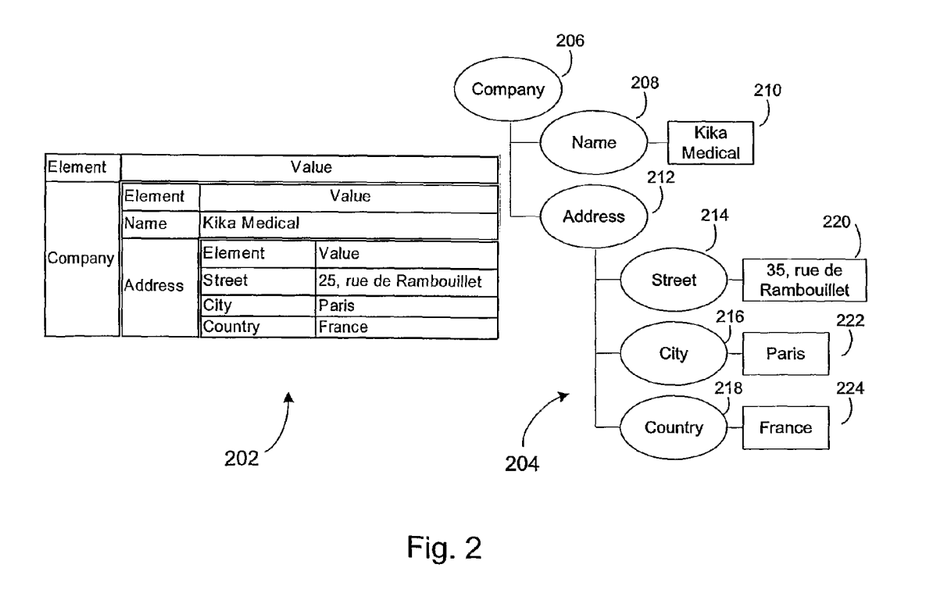
FIG. 2 is an example of the model data and diagram of FIG. 1 to which hierarchical relationships have been added.

There are numerous ways the data comprising the value of an element may be represented. For example, as shown in FIG. 1, values may be associated with elements in Java objects, illustrated in table form in table 102. An element that has a value associated with it is represented in an objectobject. In the Java object represented by table 102, element "Name" has value "Kika Medical". Other elements and associated values represent an address. In the corresponding block diagram 104 of the same data, elements are represented by ovals 106, 110, 114, and 118, while data values are represented by rectangles 108, 112, 116, 120. In a hierarchical data model, as shown in FIG. 2, one element in an object may have as its value additional elements, which in turn may have values or contain still additional elements. For example, an object represented by table 202 corresponds to a hierarchical data model 204, in which the element "Company" 206 has as its value sub-elements "Name" 208 and "Address" 212. The sub-element "Name" has value "Kika Medical" 210 while the sub element "Address" has additional sub-elements 214, 216, and 218 corresponding to the parts of the address, each with appropriate values 220, 222, 224. In some cases, the value of an element may be represented by binary data, for example, a digital image. Possible implementations of such a feature are discussed below. Other data formats can be used, such as comma-separated value files, spreadsheets, or databases. The elements and values of the data model could similarly be represented by XML tags or other data formats.

A data model can be very complex, containing a large amount of information. As a clinical study advances or a patient receives ongoing medical care, the data model is continually updated so that it always represents the current status of all aspects of the subject matter. Whenever new information is available, it is added to the data model. If a user needs current information about some aspect of the modeled information, they use a client to access the model and find the current state of the relevant data. For example, when new information concerning a patient is available, a doctor will add those results to the model. If the doctor needs to see the patient's records, he uses a client to access the model and retrieve those records.

In some examples, the data model is an extension of the Clinical Data Interchange Standards Consortium (CDISC) Operational Data Modeling (ODM) standard, which documents a hierarchical structure of clinical data elements. One part of each ODM file, known as the metadata, describes the data collected in a study. The metadata consists of definitions, with one type of definition for each of five data levels:

| | Data Level | Definition Type |
|---|---|---|
| 1 | SubjectData | Protocol |
| 2 | StudyEventData | StudyEventDef |
| 3 | FormData | FormDef |
| 4 | ItemGroupData | ItemGroupDef |
| 5 | ItemData | ItemDef |

The first four levels are container levels while the last level is for actual data values. Container definitions are lists of references, which are pointers to other data definitions. For example, the metadata defining an ItemGroupData-level element Demographics may contain references to ItemDefs Birth_Date and Patient_Sex, indicating that the Demographics element contains two sub-elements at the ItemData level, and these sub-elements are defined according to the Birth_Date and Patient_Sex item definitions and will contain the corresponding data. The item definitions at the ItemData level describe the type of data stored in the defined element, such as text, integer, float, date, etc. In the preceding example, the item definition Birth_Date would indicate that the value must be of type "date."

The CDISC standard defines two important elements, Repeating and Mandatory. Repeating, applicable to definitions, indicates whether an element can be included more than once. For example, a StudyEvent-level element Adverse_Event, defined by a StudyEventDef definition, may be repeated several times in a study, so the definition of Adverse_Event would include the element Repeating with a value "true." Mandatory is applicable to references and indicates whether a referenced sub-element is mandatory.

Transactions

The contents of a data model are changed by a transaction. A transaction may consist of instructions to add or remove elements, change the values of elements, or change the relationships between elements, such as their arrangement in a hierarchy. A single transaction may contain instructions to make multiple changes to the data model. For example, a transaction may instruct the data model to change the "Name" element of a particular person and add a "Telephone" element for that person. A transaction can be a data structure consisting of a subset of the elements of the data model it is intended to change. The values of the elements in the transaction could indicate explicit instructions, such as to add or delete an element. Alternatively, the values of the elements in the transaction could differ from the values already associated with the elements in the data model, such that the differences constitute instructions to change the values in the model accordingly.

Figure 3:
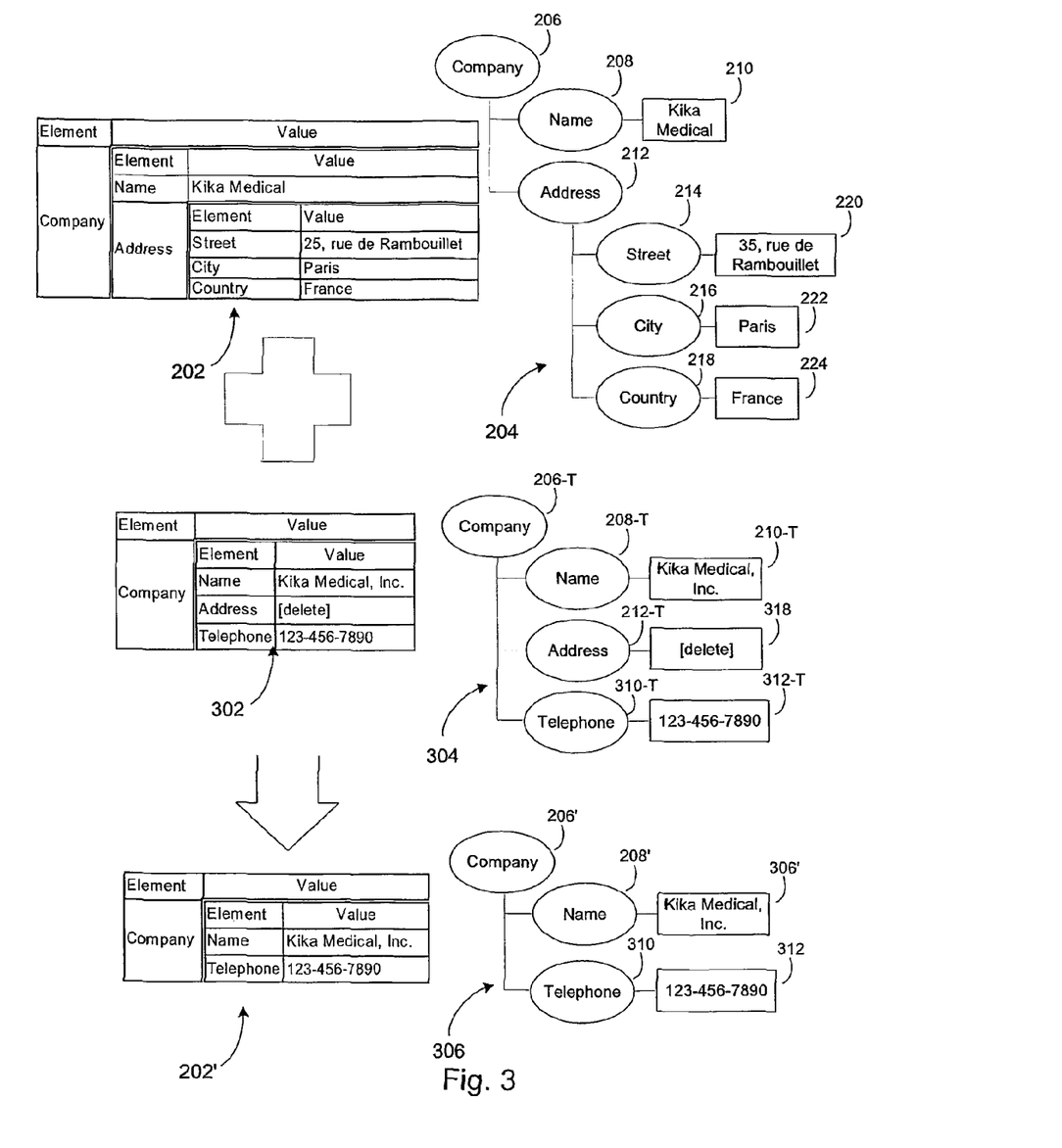
FIG. 3 is a flow diagram of illustrating a transaction starting with the model data table/diagram of FIG. 2 and making changes specified in a second model data table/diagram resulting in a third model data table/diagram.

A transaction may be represented in the same format as the data model itself. In some examples, as shown in FIG. 3, a transaction is represented by a Java object as illustrated in table 302 and the data model is stored in memory is a comparable format. Block diagrams 204, 304, and 306 illustrate the transaction and data model abstractly. A transaction consists of a set of elements in the object of table 302 corresponding to the object 202 representing the data model. The "Name" element 208-T has a different value 210-T than the corresponding element in the data model, so the transaction is regarded as an instruction to change the value of the "Name" element 208 in the data model. The "Address" element 212-T has a value consisting of the command "[delete]" 318, so the "Address" element 212 will be removed from the data model by deleting the corresponding element from the Java object. The "Telephone" element 310-T and its value 312-T are not found in the existing data model, so a new element and its value 312 will be added to the Java object. These changes are applied to the data model represented by the Java object illustrated in table 202 to produce an updated Java object, illustrated in table 202', with updated "Company" and "Name" elements 206' and 208', a new value 306' for the name element 208', and new "Telephone" element 310 having value 312.

In some examples, a minimum set of elements and corresponding values must be included in every transaction. Such elements may include a global unique identifier (GUID) (assigned by a system that processes the transactions), the date of the transaction, the user ID of the author of the modification, a reason for the modification, the GUID of the previous transaction, and references to binaries, if any. A transaction may implicitly indicate when data is to be added or changed, simply by including the new data, or it may be required in a particular implementation to explicitly indicate for each element referenced whether data is being added, changed, or deleted.

Implementation of the Model

Figure 4:
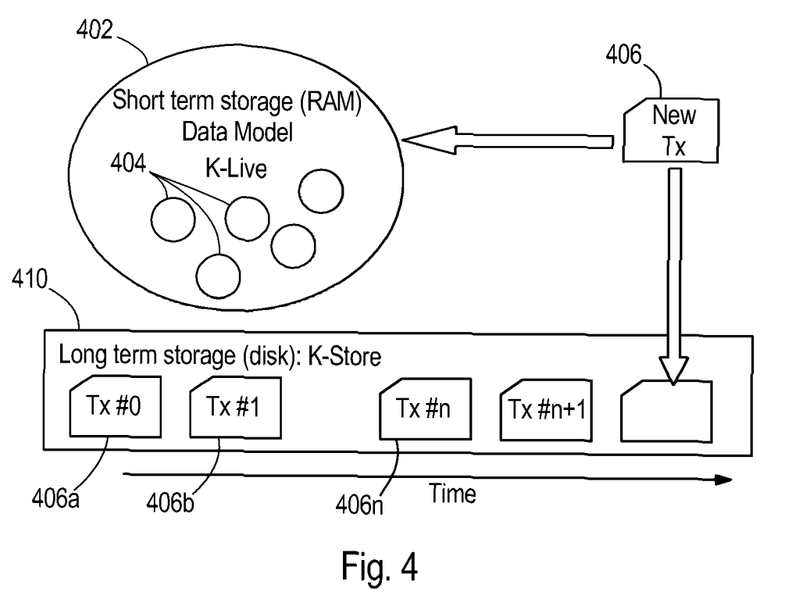
FIG. 4 is a block diagram of the input of a transaction simultaneously into a data model and into a long-term storage.

Two different components are used to store the data model in a complementary manner, as shown in FIG. 4. The short term storage 402 runs as an application on a computer system and maintains a representation of the current state of the data model. The model 404 consists of data in memory representing each element and its current value. By applying the instructions of each transaction to the data model currently in memory as the instructions are received, the representation of the model in the short term storage always represents the current state of the data model as of the most recent transaction, and can be quickly accessed to determine what that state is. When a new transaction 406 is received, the short term storage 402 analyses the transaction to determine what changes are to be made to the data model, and it makes those changes to the representation of the model 404 currently in memory. The short term storage may be limited for technical or other reasons. For example, if the data representing the current state of the data model is stored in volatile memory, that data will be lost if the computer hosting it is shut down. Storing the data in volatile memory may have advantages, such as allowing faster access to current information about the state of the data model to users or other processes that may require such information. The data representing the model could also be stored in a non-volatile memory, such as a hard disk or flash memory, with advantages and disadvantages corresponding to elements of the technology used.

The long term storage component 410 also runs, on a computer system, which may be the same system as the one running the short term storage 402, or may be separate. It stores each new transaction 406 as it is received, without analyzing the transaction or applying it to the data model. Transactions are associated with a sequence value indicating the order in which they were received. A sequence of transactions 406a, b, etc. is referred to as a "series." When it is desired to reconstruct the current state of the data model, for example, after the server hosting the short term storage has been rebooted, this is done by starting with an empty model, containing no elements or a default set of elements, and then loading a series of transactions from storage and applying them to the data model according to their sequence numbers to reproduce the process that led to the present state of the data model. Because conditions external to the data model may change between the time a transaction is stored and the time it is used to recreate a change to the data model, it is desirable that the data values in a transaction contain actual values, rather than references to external parameters. For example, if an element is to have a value representing the date on which it was stored, the corresponding value in the transaction needs to represent the actual date, i.e., "1 Jan. 2006," not a pointer to that value in a computer system, for example, the system clock, which may change, even though such a pointer would have been sufficient on the day the transaction was stored.

To assure the consistency of the current state in the short term storage and the sequence of transactions to reproduce that state in the long term storage, each transaction is applied to the current state and stored in long term storage substantially in parallel. If a transaction is applied to the current state and not stored in the long term storage, and the current state is then reconstructed from the stored sequence of transactions, the reconstructed state will not match the previous current state. Likewise, if a transaction is stored but not applied by the short term storage, the current state in memory will not represent the actual state of the project.

The storage of individual transactions and information about the order in which they were applied to the model provides several benefits. It effectively gives the model a time dimension, allowing a user to look back in time and reconstruct the model as it was at any point. This allows retrieval of the state of any part of the model at some point in time, and traceability of how the model evolved. For example, a researcher can see how the data describing a particular patient changed over time. In the example of a clinical study, a model can contain not only the data collected in the course of the study, but all information pertaining to the study, including test procedures, policies, forms, i.e., the entire protocol. The transaction storage system allows this information to also be reconstructed, for example to determine whether intake questions were changed after some patients had already started the trial. Without such traceability, costly and time-consuming computations may be required to discover such a fact.

This traceability also allows statistical analysis of the entire population of a study at any historical point in time. The state of the model can be recreated, by replaying all the transactions up to that point, and then the model as of that point used as the source of data for analysis. If the analysis concerns only a subset of the population, or only a particular symptom, only the transactions affecting the relevant population or symptom need to be replayed, allowing for even faster reproduction and extraction of the needed data.

Auditing is also improved by this model and transaction system. For example, in a clinical trial, the death of a patient requires that the trial stop. If it is learned that a death occurred and the trial continued, auditors can use the transaction history to rebuild the model as it stood at the time of the death to see what else was going on, who was aware of the situation, and why the trial was not halted. Such auditing using the traceability provided by the transaction history can also reveal fraud, misrepresentations, and defective data.

Tools to Maintain and Use the Model

Figure 5:
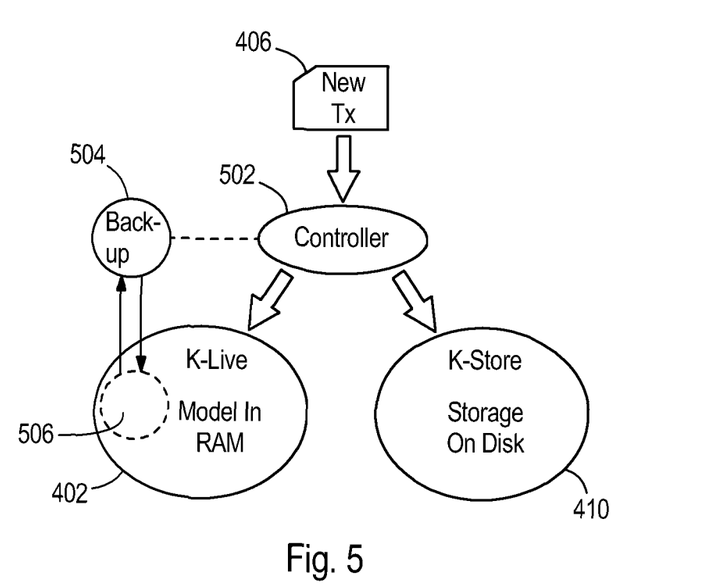
FIG. 5 is a block diagram of a controller handling the flow of a transaction to the components shown in FIG. 4.

As shown in FIG. 5, a controller module is another software application, and is configured to manage the flow of transactions from clients that access the data model. It may or may not operate on the same computer system as the other components. When a transaction 406 is received, a controller 502 checks it against a set of rules to confirm that the changes it instructs to the data model are valid. The controller then provides the transaction to both the short term storage 402 and the long term storage 410 for appropriate handling. To insure reliability, the controller analyses the changes that will be made by the transaction and makes a backup copy 504 of the part 506 of the data model, as represented in the current state, that is about to be modified by the transaction. The controller may be configured to backup a larger part of the data model than will clearly be affected by the changes, to assure that the backup is adequate. The transaction is then applied to the model by the short term storage 402, generating a new revision and current state. The state may then be checked against a set of rules to assure that the revised data model continues to comply with them. If a rule is violated, the transaction is rejected and the backup is used to restore the data model to the state that existed before the revision. If no rule is violated, then the controller 502 instructs the long term storage 410 to store the transaction. If for some reason the storage of the transaction is not successful, then the backup 504 is again used to restore the data model to its previous state. Even though no rules were violated by the changes, since they were not stored, the revised state will not be recreated when the sequence of transactions is again applied, so the current state should not reflect the new changes.

The controller also regulates access to the data model to prevent any inconsistencies. When a transaction is received, the controller applies a lock such that only a request handler handling the current transaction can modify the data model. This prevents other clients from submitting transactions to change the model at the same time. Once the transaction is stored, the lock is withdrawn. Likewise, when a client is reading the model, the controller may apply a read-only lock so that other clients may also read the model, but none will be able to change it while it is being read.

Long Term Storage Component

Figure 6:
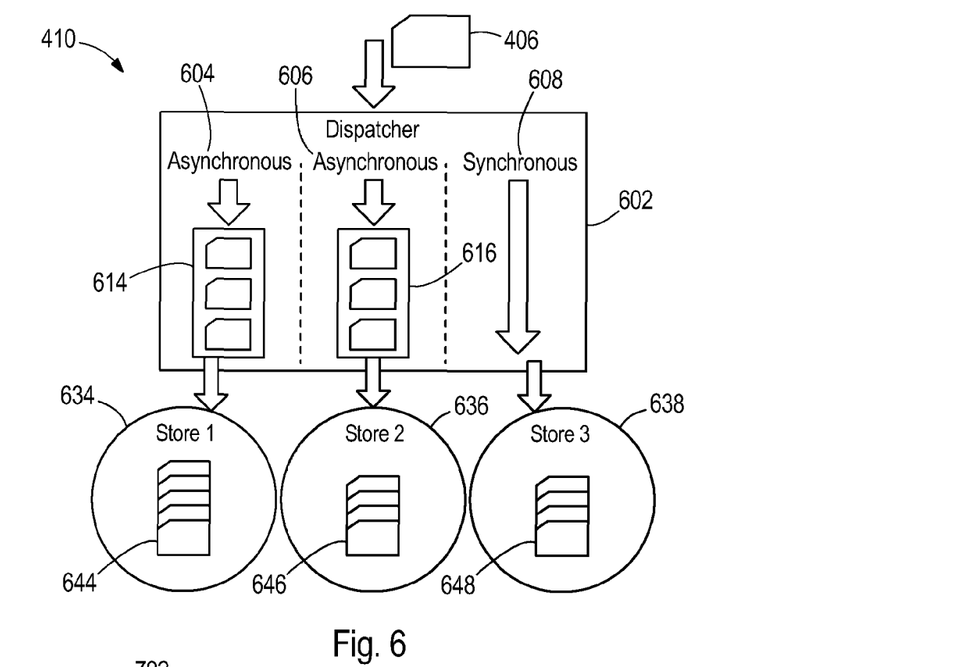
FIG. 6 is a block diagram of a detailed embodiment of the long-term storage of FIG. 5.

The long term storage component is made up of two layers: the dispatcher and storage for series of transactions, as shown in FIG. 6. The sequences of transactions comprising each series may be stored on a single server or on multiple servers, depending on the needs of the system. Servers storing the transactions may be integrated with the dispatcher or other components, or may be remote, or both. The dispatcher 602 receives transactions 406 that have been accepted by the controller and applied to the corresponding data model and adds them to the appropriate series. Several instances 604, 606, 608 of a particular series may be maintained for backup purposes, such that a problem with one instance will not fatally jeopardize the integrity of the data model. Each instance may be stored in a separate storage location 634, 636, 638. The dispatcher 602 monitors the state of each instance. If the storage fails to add a transaction to an instance of a series, the dispatcher identifies that instance as no longer available, since writing any additional transactions to it might break the integrity of the sequence represented by that series.

Instances of series may be synchronous or asynchronous. A synchronous instance 608 writes each transaction to its corresponding storage location 638 as it is received, with the dispatcher waiting for each write operation to complete before sending the next transaction. Asynchronous instances 604, 606 use queues 614, 616 of transactions to be stored in a first-in, first-out manner in corresponding storage locations 634, 636. The dispatcher 602 sends transactions to each queue as the transactions are ready, and the corresponding storage location takes them from the queue and writes them to the stored instance 644, 646 of the series as fast as it is able. Synchronous instances tend to provide slower access to the data, as the system has to wait until the storage operation is completed before moving on to the next one. Asynchronous instances can allow faster response, allowing the system to move on while the storage is being executed, but may be less reliable. A typical installation will have at least one synchronous instance, since it is important to have at least one reliable transaction history always available. The choice of how many of each kind to use will depend on the reliability and performance requirements and available resources of a particular implementation.

Queues may have a limited size, in which case, if a queue fills up, the dispatcher may have to stop sending, transactions to the corresponding instance, possibly interrupting the sequence of transactions in that instance. When the dispatcher has stopped writing to an instance because its sequence of transactions has been interrupted, it may later be able to use a synchronizing tool to synchronize the series in that instance with another that was not interrupted so that the instance may be returned to service. The synchronizing tool reads from a valid instance the transactions that are missing from the interrupted series and inserts them into that instance of the series until it is up-to-date. This process could be automated by equipping the storage component with the ability to draw transactions from one instance and write them to other instances to assure that each stays up to date without the dispatcher having to monitor each instance's status.

The details of how a sequence of transactions constituting a series is stored will vary according to the format of the transaction. In one example, a transaction is represented by an XML file, and a series comprises a set of such XML files. Each transaction file may contain a tag representing the sequence number of the transaction. Alternatively, a separate list of the order of transactions in a particular series may be maintained, using unique identifiers associated with each transaction. If a value of an element in the data model is to include a binary file, which is not ordinarily accommodated by the file type of the transaction, as is the case with XML, the transaction may include an identification of the binary file, with the binary file maintained in a separate file.

Figure 7:
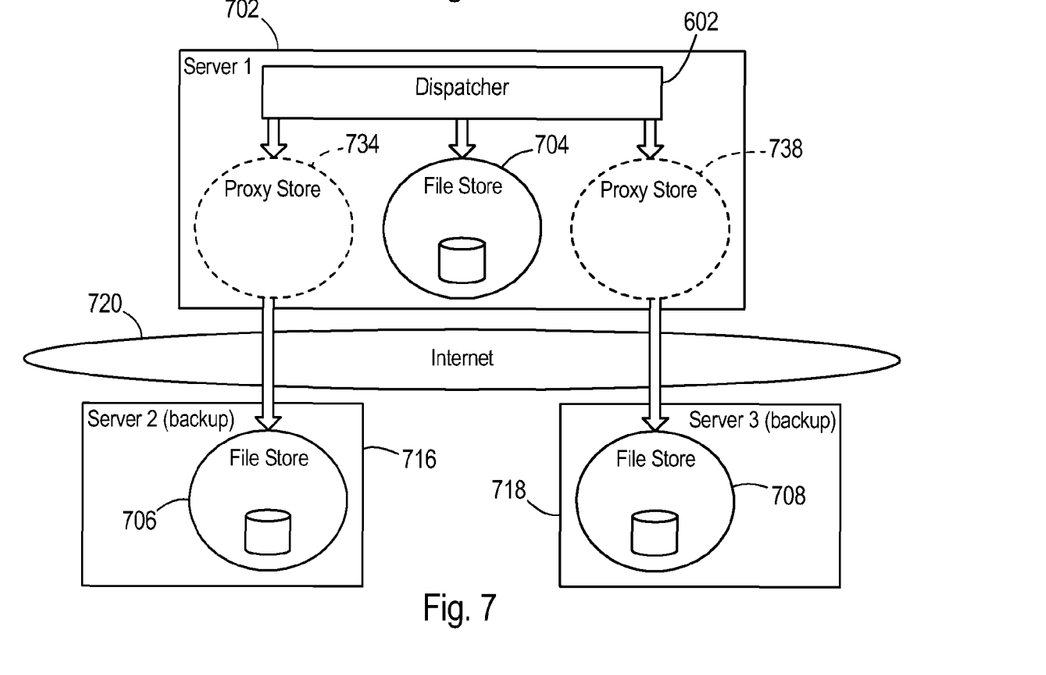
FIG. 7 is a block diagram of a computer system for carrying out the storage system of FIG. 6.

In one example, as shown in FIG. 7, an instance 704 of a series is stored locally in a directory of the file system of the server 702 hosting the dispatcher 602. The layout of the storage directory and the file system can be optimized for reliability and speed. Setup of such an arrangement may require only that the file system of the host computer have available resources.

In another example, also shown in FIG. 7, instances 706, 708 of a series are stored in remote file systems on servers 716, 718. Commands to store, configure, or access stored instances can be sent to the remote file systems over the a network 720, for example, using HTTPS or other protocols. Commands may also be sent using a dedicated data connection between the local system hosting the dispatcher and the remote file system, using a virtual private network or other Internet connection, or in other ways. Using a remote file system allows that file system to differ from the file system used by the local computer. It may be advantageous to use an asynchronous instance on a remote file system due to latency of the network communications. Proxies 734, 736 for instances 706, 708 stored on remote file systems may be configured in the local server 702, for example, so that the dispatcher 602 can access the stored instances as if they were local without being required to be configured according to the details of the file systems used on the remote servers 716, 718.

Additional Features

Figure 8:
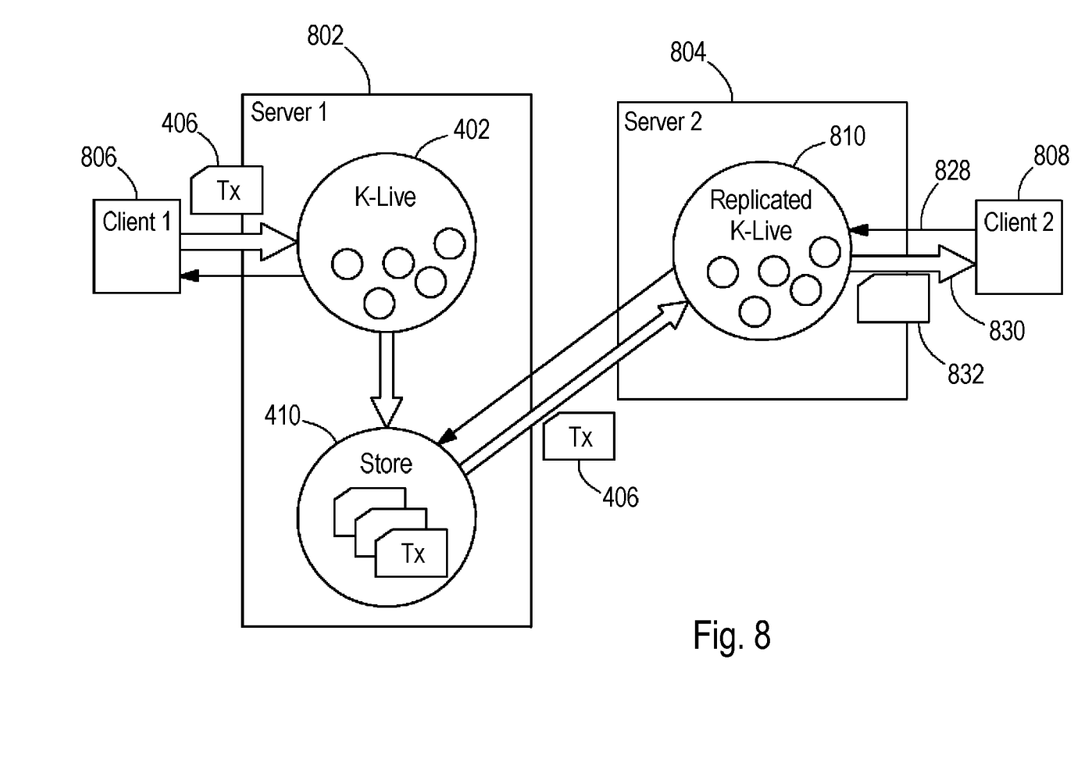
FIG. 8 is a block diagram of a computer system for replicating the model component of FIG. 5.

In one example, shown in FIG. 8, an additional server 804 maintains a duplicate of the current state of the data model, which is maintained in short term storage 402 on a server 802. The additional server 804 reads transactions stored in the long term storage component 410 and applies each transaction to the locally-maintained duplicate 810 of the data model. To make changes to the data model, a client 806 must send a transaction to the primary server' 802. The client can retrieve information about the current state of the model from the short term storage as usual. Periodically, the additional server 802 requests new transactions from the long term storage 410 on server 802. If any new transactions have been incorporated into the model since the last request, such transactions are transmitted to the server 802 and incorporated into the duplicate model 810. A client 808 can access the duplicate model for purposes that only require read access, such as gathering statistics or reporting on the state of the data model. Data 832 is transmitted to the client 808. Such an arrangement may reduce communication latency for clients that have a more direct connection to the additional server 804 than to the primary server 802. It may also reduce the load on the primary server, as fewer clients will require its resources. It may also improve the integrity of the data model, for example by allowing certain clients to only access the secondary server, such that they can never make changes to the model.

Figure 9:
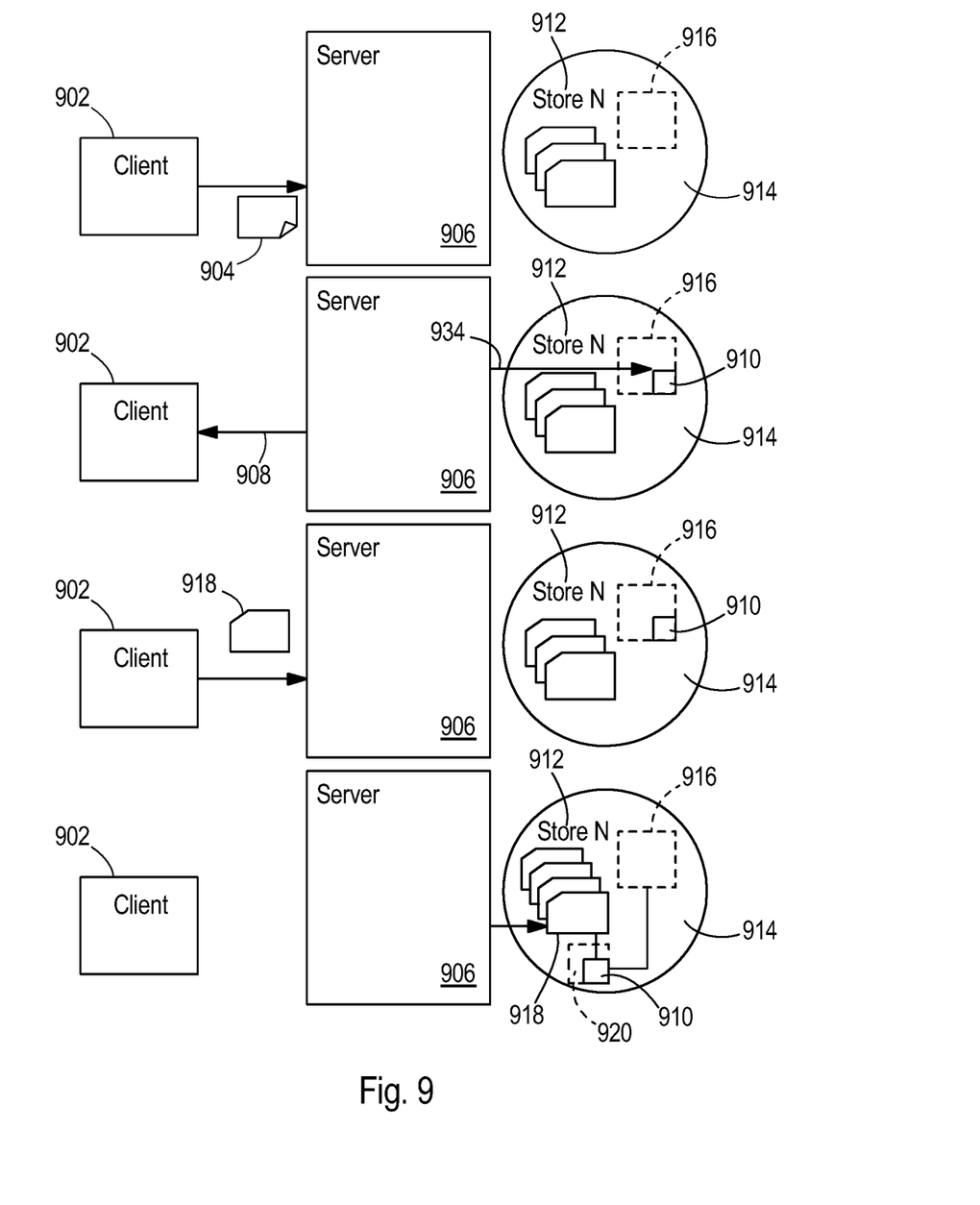
FIG. 9 is a block diagram of another embodiment of the long-term storage of FIG. 5.

In one example, as shown in FIG. 9, if a client 902 needs to add a binary file 904 to the data model, it uploads the binary file to the server 906 hosting the controller (not shown). The server assigns a unique identifier 908 to the binary file, similar to identifiers assigned to transaction files, and sends a copy 910 of the file to the storage locations 914 responsible for each instance 912 of the series that will contain the corresponding transaction. The storage locations 914 each place the binary file 904 in a temporary storage location 916. The server then communicates the identifier 908 of the binary file to the client. The client then sends a transaction 918 as an XML file, with one tag representing the binary file and containing the identifier of the file as its value. If the transaction is successfully added to the data model by the short term storage (not shown), it is sent to the long term storage (not shown) in the same manner as any other transaction. Each storage location 914 for an instance of the series that receives the transaction 918 referencing the binary file 904 looks for the binary file in its temporary binary location 916 and moves it to a permanent location 920. If the file is not found, the transaction fails and is removed from the data model as with any other failed transaction. The insertion of the transaction into at least one instance of the series and the moving of the binary into the permanent storage of the corresponding storage component are handled as a single operation to assure consistency. If a single binary file is referenced by more than one transaction, only a single copy of the binary needs to be placed in permanent storage. When a transaction is received referencing such a binary file, the transaction is added to the series as normal with no additional steps required.

Figure 10A:
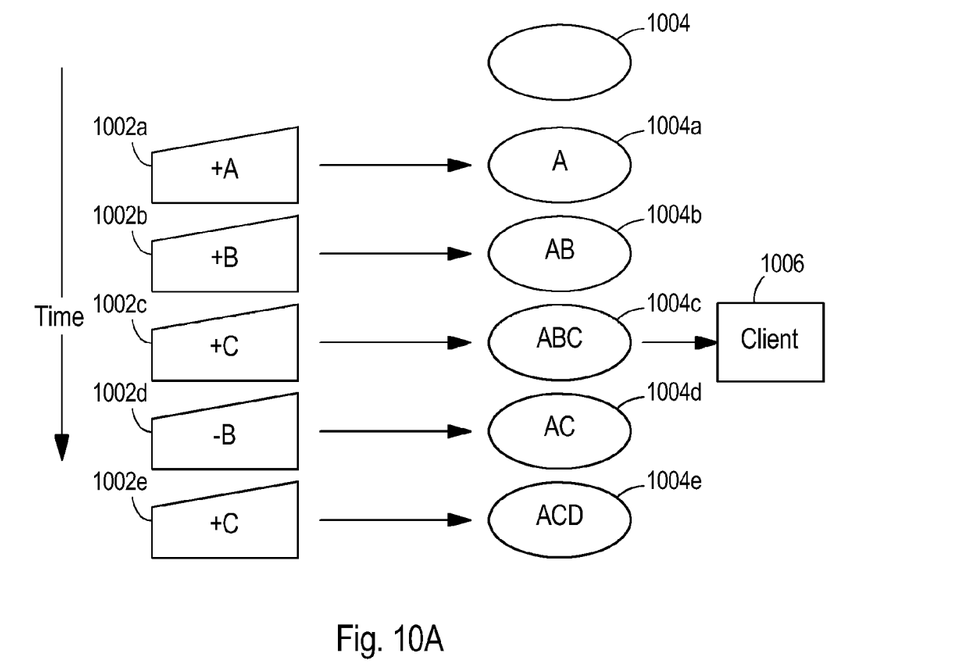
FIGS. 10A and 10B are block diagrams of a detail of steps in the operation of the model component of FIG. 5.
Figure 10B:
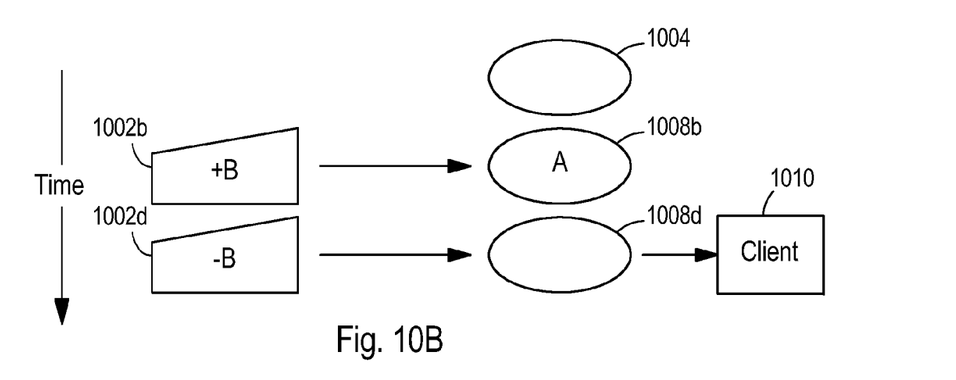

Since the stored sequence of transactions is used to recreate the current state of the data model each time the short term storage is loaded, it is easy to recover older versions of the model. For example, as shown in FIG. 10A, the process of recreating the model can proceed as normal, starting with an empty model 1004, with transactions 1002a-e resulting in revisions of the model 1004a-e. If a client 1006 wants to know what was in the model at a specific time, for example the time transaction 1002c was entered, the reconstruction can be halted after that transaction is applied, and a copy of the corresponding revision of the model 1004c sent to the client. Similarly, as shown in FIG. 10B, if a client 1010 is interested in only a subset of the data represented by the model corresponding to element B, the current state or any revision state of that data may be recreated without recreating the entire data model. This is accomplished by applying only those transactions 1002b and 1002d that affect the element B, creating reduced versions of the model 1008b and 1008d, thus saving processing time and memory required to store the model. Because the transactions can be represented as versions of the data model containing only data relevant to the changes made by that transaction, they can be easily filtered to find the set of transactions necessary to see the current state of any subset of the data model. For example, a set of elements in the model may represent a Form A with information pertaining to a patient X, while other sets of elements may represent copies of Form A with information about other patients. The set of transactions that modify sub-elements of Form A for patient X can be applied to reconstruct only the Form A for that patient, without reconstructing copies of Form A for other patients or any parts of the model.

Figure 11:
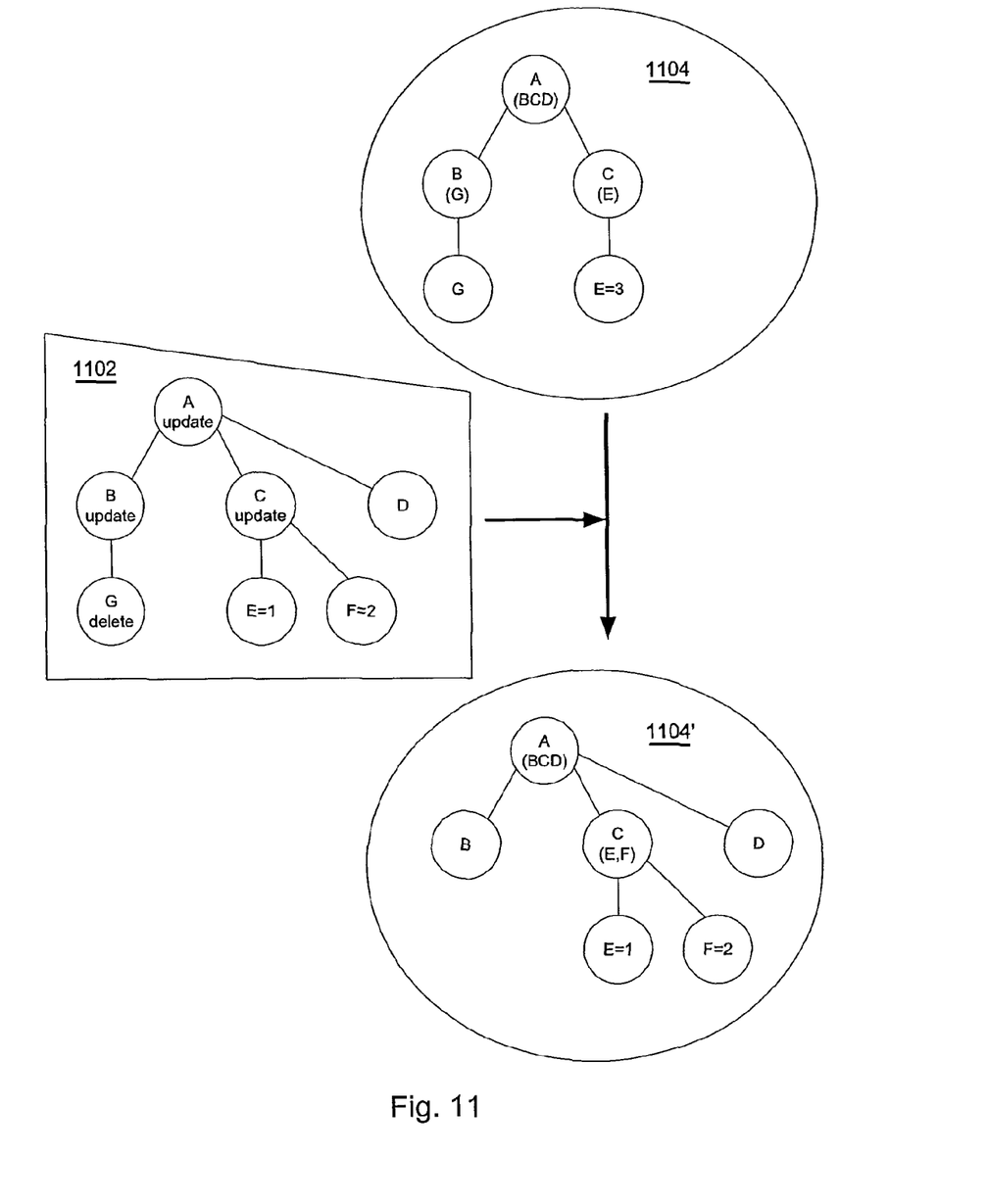
FIG. 11 is a block diagram of an embodiment of one step of the process of FIGS. 10A and 10B.

If the data model is organized hierarchically, handling of elements in transactions may be more complex. For example, as shown in FIG. 11, in a hierarchical arrangement, elements may be categorized as ancestor or child nodes, e.g., nodes A and E, respectively, and a given node could be of both types simultaneously, e.g., node C, which is a child of node A and an ancestor of node E. A transaction 1102 must contain elements corresponding to each ancestor of any child nodes it modifies. For example, if child nodes D and F are added, all of their ancestors, A and C, must be present in the transaction and marked either to be inserted themselves or to be updated to recognize the child. If a child node E is modified, all of its ancestors are marked to also be modified. If a child node G is deleted, all of its ancestors, nodes A and B are marked either to be deleted or to be updated. All the changes in transaction 1102 are applied to the present revision of the model 1104 to produce a revised version 1104'.

Elements pertaining to the hierarchy are included in each node to facilitate model reconstruction and history recovery. In one example, these elements include the GUID of the last transaction that inserted or updated any children of the node and the date that transaction was executed. With these elements, the system can rapidly discover which is the last transaction that modified a data node and from that, find who made the modification and whether other nodes were modified at the same time. For example, if a node corresponds to a particular patient, a user may want to know who was the last researcher to update that patient's information, and which other patients' information did that researcher alter at the same time. The node for that patient, which will be a parent node for nodes representing information about the patient, will contain the GUID of the last transaction that modified that patient node or any of its children nodes. That transaction can be retrieved based on its GUID, and the researcher who initiated it identified.

A number of embodiments of the invention have been described. Nevertheless, it will be understood that various modifications may be made without departing from the spirit and scope of the invention. For example, a last-current copy of the model may be maintained in long-term storage to facilitate rebuilding the active model. Accordingly, other embodiments are within the scope of the following claims.

What is claimed is:

1. A computer-implemented method of managing healthcare data relating to a clinical trial, the method comprising:
   storing, in a first storage component, a data model having elements and associated values;
   receiving, by a controller module, a transaction;
   generating a revised data model by implementing the received transaction and storing the revised data model in the first storage component; storing the transaction and information regarding an order in which the transaction was implemented to each of a plurality of sequences of transactions in at least one second storage component;
   determining whether the transaction and the information regarding the order is successfully stored to each of the plurality of sequences of transactions;
   when the transaction and the information regarding the order is not successfully stored to one of the plurality of sequences of transactions, identifying the one of the plurality of sequences of transactions as invalid;
   identifying from at least one of the plurality of sequences of transactions not identified as invalid a set of transactions implemented between an empty state of the data model containing no elements and prior to implementing the received transaction; and
   applying the identified set of transactions to an empty data model containing no elements to reconstruct the data model prior to implementing the received transaction.

2. A system for managing healthcare data relating to a clinical trial, the system comprising:
   a computer including non-volatile memory storing a controller module;
   the controller module configured to:
   store a data model having a plurality of elements and associated values in a first storage component;
   receive a transaction from the controller module;
   generate a revised data model by implementing the received the transaction; store the revised data model in the first storage component;
   store the transaction and information regarding an order of the transaction to a first sequence of transactions in a second storage component and store the transaction and the information regarding the order to a second sequence of transactions in a third storage component;
   receive from a user a selection of at least one of the plurality of elements and a requested historical point in time;
   identify from the at least one sequence of transactions a set of transactions associated with only the selected at least one element and implemented between an empty state of the data model containing no elements and the requested historical point in time;
   apply the identified set of transactions to an empty data model containing no elements to construct a reduced data model including only data relevant to the selected at least one element; and
   provide the reduced data model to the user.

3. The system of claim 2, wherein the transaction is stored in parallel with generating the revised data model.

4. The system of claim 2, wherein the controller module is further configured to:
   determine whether the transaction and the information regarding the order is successfully stored to the first sequence of transactions and the second sequence of transactions; and
   when the transaction and the information regarding the order is not successfully stored to one of the first sequence of transactions and the second sequence of transactions, identify the one of the first sequence of transactions and the second sequence of transactions as invalid.

* * * * *